United States Patent [19]

Narayanan

[11] Patent Number: 5,684,121
[45] Date of Patent: Nov. 4, 1997

[54] N-VINYL LACTAM POLYMER CONTAINING TABLETS OF LOW FRIABILITY AND HIGH RATE OF DISSOLUTION

[75] Inventor: Kolazi S. Narayanan, Wayne, N.J.

[73] Assignee: ISP Investments Inc., Wilmington, Del.

[21] Appl. No.: 349,774

[22] Filed: Dec. 6, 1994

[51] Int. Cl.$^6$ .......................... C08G 63/00; C08G 73/10; A61K 9/00
[52] U.S. Cl. .......................... 528/363; 528/310; 424/470; 424/482; 424/489; 424/501
[58] Field of Search .................................. 424/470, 482, 424/489, 501; 528/310, 363

[56] References Cited

U.S. PATENT DOCUMENTS

| 5,137,730 | 8/1992 | Dennis et al. | 424/470 |
| 5,200,193 | 4/1993 | Radebaugh et al. | 424/470 |
| 5,242,684 | 9/1993 | Merianos | 424/501 |
| 5,326,572 | 7/1994 | Mehra et al. | 424/470 |
| 5,354,560 | 10/1994 | Lourecich | 424/501 |
| 5,405,412 | 4/1995 | Willey et al. | 8/111 |

*Primary Examiner*—Samuel A. Acquah
*Assistant Examiner*—P. Hampton-Hightower
*Attorney, Agent, or Firm*—Marilyn J. Maue; Walter Katz; Joshua J. Ward

[57] ABSTRACT

This invention relates to a coprecipitated binder composition used for the compression of pharmaceutically and agriculturally active components to provide a non-friable, readily soluble or dispersible pill or tablet. The invention also relates to the process for preparing the binder and to its incorporation in a formulation with the active ingredient.

8 Claims, No Drawings

N-VINYL LACTAM POLYMER CONTAINING TABLETS OF LOW FRIABILITY AND HIGH RATE OF DISSOLUTION

DISCUSSION OF THE PRIOR ART

Pharmaceutical and agricultural compositions containing polymeric lactam carriers or binders have been found wanting in several respects. Either they have exhibited undesirable friable properties when subjected to high compression, thus causing difficulties in packaging and shipping as well as increasing costs due to losses of uniform tablet size with accompanying accuracy in prescribed dosage levels or else the compositions are characterized as having a low rate of dissolution which seems to vary directly with the degree of compression since the forces imposed during manufacture compresses the lattice structure thus causing poor liquid penetration. Undesirable rates of dissolution are particularly recognized where vinyl lactam copolymers are employed as binders in the agrichemical and pharmaceutical compositions.

Accordingly, it is an object of the present invention to provide a binder for use in pharmaceutical and agricultural chemical formulations which markedly increases the rate of tablet dissolution while retaining a high lattice energy matrix resistant to crumbling or powdering during the packaging process.

Another object of the invention is to provide a binder material which reduces the number of components needed in the production of readily dissolvable pills and tablets.

Still another object is to facilitate the manufacture of tablets having the above improved properties by a simple and economical process.

These and other objects of the invention will become apparent from the following description and disclosure.

THE INVENTION

In accordance with the present invention there is provided a composition containing a medically or agriculturally prescribed amount of the respective active chemical and a binder comprising a polymer of an N-vinyl lactam containing from 4 to 6 ring carbon atoms and an organic polybasic carboxylic acid combined in a mole ratio of polymer to —COOH group of between about 1:0.1 and about 1:10, preferably between about 1:0.5 and about 1:4.

The N-vinyl lactam polymers of the invention include both homopolymers and copolymers with one or more comonomer selected from the group including a vinyl ester, such as for example vinyl acetate, vinyl ethylate, a $C_1$ to $C_4$ alkyl-acrylate or methacrylate; a $C_3$ to $C_{12}$ alpha-olefin, such as for example 2-propene, 3-butene, 7-octene, 9-decene, 11-dodecene; an N-vinyl amide, such as for example N-vinyl succinamide, N-vinyl adipamide and an N-vinyl imide such as N-vinyl succinimide. The N-vinyl lactam monomer can be unsubstituted or substituted on a ring carbon atom with a $C_1$ to $C_4$ alkyl group. Such lactam monomers are exemplified by N-vinyl pyrrolidone, N-vinyl caprolactam, 3-methyl N-vinyl pyrrolidone, 3,4-dimethyl N-vinyl pyrrolidone, ethyl N-vinyl caprolactam, 3-butyl N-vinyl pyrrolidone etc. and can be used as lactam mixtures, such as for example a mixture of N-vinyl pyrrolidone and N-vinyl caprolactam. For the purposes of this invention, the unsubstituted lactam monomers are preferred and N-vinyl pyrrolidone or mixtures of N-vinyl pyrrolidone and N-vinyl caprolactam are most preferred. In general, the polymers of the present invention contain from about 40 to 100 wt. % N-vinyl lactam monomer and are water soluble or water dispersible polymers having a number average molecular weight between about 2,500 and about 1,000,000. These polymers, in their compressed form, are characterized as having undesirably slow dissolution rates and are subject to crumbling or powdering due to attrition when packaged in bundles.

Suitable polybasic acids of the invention are polycarboxylic acids containing from 3 to 14 carbon atoms, which are unsubstituted or optionally substituted with hydroxy. These acids are defined by the formula

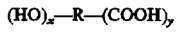

$$(HO)_x-R-(COOH)_y$$

wherein x has a value of from 0 to 4, y has a value of from 2 to 4 and R is alkylene having 1 to 10 carbon atoms. The preferred acids of this invention are the di- and tri-carboxylic acids containing from 3 to 6 carbon atoms as in adipic, citric, glutaric, malonic, malic, maleic, succinic, saccharic, saccharonic, tartaric, tricarballylic acids and the like.

The acid is coprecipitated with the polymer component forming a polymeric, hydrogen bondable complex. This condition retains the high lattice packing capability of the polymer under high compression while providing hydrogen bondable sites for minimizing friability and at the same time maximizes dissolution through the carboxyl groups to provide a formed pill or tablet suitable for packaging and readily dissolvable in water, enzymic fluid or other liquids by the consumer. The present composition also eliminates or minimizes the need for extraneous components such as surfactants, emulsifying agents, solubilizers and the like; although a buffering agent, such as an alkali metal salt or an ammonium or alkyl ammonium salt of the present acid, in an amount up to about 30 wt % of the total composition, is optionally included to maintain a pH of 5-7, depending on the end use of the tablet. For example a buffering agent may be employed to neutralize acidity or the action of stomach acids in medicinal use applications.

The present solids composition also contains an a conventionally prescribed amount of an active ingredient such as an agrichemical or pharmaceutical component which can be insoluble or difficultly soluble in water or which can possess such high water solubility that rainfastness properties are minimal. In the later case, the film forming capability of the polymer upon dissolution, enhances retention of the active component on the site of application. The active ingredient usually does not exceed 85 wt % of the total solids composition and includes a pesticide, fungicide, herbicide, plant growth regulant, nematocide, fertilizer, nutrient, bactericide, virucide or any of the drugs useful for treating pathogens, relaxant, antiacid, pain blocker, or any medication which can be administered in solid, prescribed dosage form. Mixtures of these active chemicals are also suitable in the compositions of the present invention.

The present solid compositions are economically prepared by dissolving the polymer and the acid in a mutual solvent, e.g. water, a $C_1$ to $C_4$ alcohol, glycerol, glycols or aqueous solutions of said solvents; forming the complex of the components at a moderate temperature, e.g. from about 35° C. to about 60° C., under continuous agitation over a period of from about 2 to about 8 hours followed by distillation under vacuum at below 60° C., preferably at 40°-55° C., to remove solvent and form the crystalline binder product. Alternatively, when water is employed as the solvent, it can be removed by freeze drying. The binder product is then dried and ground to an average diameter particle size of between about 20 and about 350, preferably 30–250 microns before mixing with the proper or prescribed amount of the active chemical in solid form. The resulting mixture is then compressed into pills or tablets according to conventional procedures.

Alternatively, an aqueous mixture of the polymer/acid complex can be sprayed into a preformed pharmaceutical or agricultural chemical formulation in a fluid bed mixing process preceding tabulation or granulation. The dissolution rate of the resulting tablets is increased 3 to 10 fold per 1% (measured by the number of inversions required to dissolve the polymer complex) over other tablets containing polymeric N-vinyl lactam employing other binder mixtures.

Having generally described the invention, reference is now had to the following examples which illustrate preferred embodiments and provide comparative data; however, these examples are not to be construed as limiting to the scope of the invention as more broadly defined above and in the appended claims.

EXAMPLE 1

A 5-liter round bottom flask was charged with 269.5 g Agrimer 30* (2.4 moles), 226 g citric acid (1.2 moles) and 2 liters of deionized water. The contents were stirred with a magnetic stirrer for a period of 2.5 hours at room temperature to produce a solution. The resulting solution at a rate of 150 ml was introduced into several flasks. The flasks and contents were then placed in a commercial freeze drier unit and subjected to 500 millitorr at 90° C. for a period of 24 hours. The solid materials obtained were scrapped from the flasks and ground into a fine powder in a commercial blender. The total solid recovered for testing was 470 g, the balance was left on the sides of the flask and blender. The sample was analyzed for its homogeneity and found to contain 49±0.5% citric acid. The dry sample was then separated into different particle sizes by sieving. Particles were separated into three groups: 100 mesh (150–250 microns), 200 mesh (75–150 microns), and <200 mesh (<75 microns). The number of inversions needed to dissolve 1% polymer, (i.e. about 2% complex) was found to be 10.7±1 independent of particle size.

*Polyvinyl pyrrolidone K 30

EXAMPLE 2

(Comparative Data)

(A) Example 1 was repeated using 32.7 g PVP K 30 and 28.25 g anhydrous citric acid dissolved in 550 ml of deionized water. The freeze-dried product required 11±1 inversions to dissolve 1% polymer (2% complex) in deionized water.

(B) Example 1 was repeated using 32.7 g PVP in the absence of citric acid and dissolved in 550 ml deionized water. The freeze-dried product required 66±8 inversions to dissolve 1% polymer (2% complex) in deionized water.

(C) Polyvinyl pyrrolidone, 135 g (1.2 moles PVP K 30) and 113 g citric acid (0.6 moles) were blended dry in a dry-blender and the product was separated into three particle size groups as above. The dissolution rate of these samples was determined. The number of inversions were found to be erratic, varying between 9–39 inversions required to dissolve 1% polymer (2% product). Analysis of citric acid content also showed a wide variation between 30–77% indicating the sample to be heterogeneous.

Examples 1 and 2 illustrate the advantage of freeze-drying the aqueous solutions containing the coprecipitated components.

EXAMPLE 3

3A A 1-liter round bottom flask was charged with 31.3 g vinyl pyrrolidone/vinyl acetate copolymer (Agrimer VA 6—PVP VA 630), 29.7 g anhydrous citric acid and 550 g ethanol. The charge was heated under a stream of nitrogen at about 60° C. for a period of 4 hours. The ethanol was removed by a rotary evaporator under reduced pressure, so that the temperature was below 60° C. The solid that was separated was ground in a dry blender and separated into three portions, i.e. 100 mesh (150–250 microns), 200 mesh (75–150 microns), and about 180 mesh (up to about 70 microns), using U.S. standard sieves.

3B (Comparative Example)

A dried 31 g sample of vinyl pyrrolidone/vinyl acetate copolymer (Agrimer VA 6—PVP VA 630) was prepared as above except that citric acid was omitted. This sample was similarly separated into three particle size groups via sieving as above. The dissolution rates for samples A and B are shown below in Table I.

TABLE I

| Ex. | Particle Size | Average No. of Inversions |
| --- | --- | --- |
| 3A | 150–250 microns | 9.7 ± 1.5 |
| 3A | 75–150 microns | 20.0 ± 6.0 |
| 3A | <70 microns | 18.0 ± 6.0 |
| 3B | 150–250 microns | >147 |
| 3B | 75–150 microns | 122–166 |
| 3B | <70 microns | 146–202 |

EXAMPLE 4

4A Example 3A was repeated using 31.95 g vinyl pyrrolidone/butene-1 copolymer (Agrimer AL 10—Ganex P 904) in the place of Agrimer VA 6, 29.7 g anhydrous citric acid and 550 g ethanol. The charge was heated under a stream of nitrogen at about 60° C. for a period of 4 hours. The ethanol was removed by a rotary evaporator under reduced pressure, at a temperature below 60° C. The recovered solid was ground in a dry blender and similarly separated into three portions, i.e. 200 mesh (150–250 microns), 200 mesh (75–150 microns), and <200 mesh (<75 microns), using U.S. standard sieves.

4B A 31.95 g sample of the polymer vinyl pyrrolidone/butene-1 copolymer (Agrimer AL 10—Ganex P 904) was prepared as above, except that citric acid was omitted. This sample was similarly separated into three particle size groups, i.e. 100 mesh (150–250 microns), 200 mesh (75–150 microns) and <200 mesh (<75 microns) via sieving as above. The dissolution rates are shown below in Table II.

TABLE II

| Ex. | Particle Size | Average No. of Inversions |
| --- | --- | --- |
| 4A | 150–250 microns | 75 ± 8 |
| 4A | 75–150 microns | 98 ± 7 |
| 4A | <75 microns | 100 ± 6.0 |
| 4B | 150–250 microns | >180 |
| 4B | 75–150 microns | >180 |
| 4B | <75 microns | >200 |

EXAMPLE 5

5A Example 3A was repeated except that 32.7 g polyvinyl pyrrolidone, PVP K 30 in the place of Agrimer VA 6, 28.25 g anhydrous citric acid and 550 g ethanol were used. The recovered ground material was separated into three portions, i.e. 100 mesh (150–250 microns), 200 mesh (75–150 microns), and <200 mesh (<75 microns), using U.S. standard sieves.

5B Example 5A was repeated except that citric acid was omitted. The 32.7 g sample of PVP K 30 was similarly separated into three particle size groups via sieving as above and the dissolution rates are as reported in Table III.

EXAMPLE 6

Example 5A was repeated except that 38.7 g polyvinyl pyrrolidone, PVP K 30, 22.3 g anhydrous citric acid and 550 g ethanol were used. The recovered ground material was separated as above i.e. 100 mesh (150–250 microns), 200 mesh (75–150 microns), and <200 mesh (<75 microns), micron sizes and the dissolution rates reported in Table III.

EXAMPLE 7

Example 6 was repeated with 47.3 g polyvinyl pyrrolidone, PVP K 30 and 13.62 g anhydrous citric acid and 550 g ethanol. The recovered solid material was similarly separated into three portions using U.S. standard sieves and the dissolution rates are shown in Table III.

TABLE III

| Ex. | Particle Size | Average No. of Inversions | Polymer/Citric Ratio |
|---|---|---|---|
| 5A | 150–250 microns | 35 ± 20 | 2:1 |
| 5A | 75–150 microns | 42 ± 10 | 2:1 |
| 5A | <75 microns | 50 ± 14 | 2:1 |
| 5B | 150–250 microns | 91 ± 14 | 1:0 |
| 5B | 75–150 microns | >150 | 1:0 |
| 5B | <75 microns | >150 | 1:0 |
| 5 | 75–150 microns | 32–52 | 2:1 |
| 6 | 75–150 microns | 82–112 | 3:1 |
| 7 | 75–150 microns | 108–126 | 6:1 |

The coprecipitation of binder from alcohol was slower than from water; however, the residual water in the samples (2–3%) did not affect the dissolution rates of the products.

EXAMPLE 8

Example 2A was repeated except that higher molecular weight PVP K 90 replaced PVP K 30. The dissolution rate was about 60 inversions for 1% polymer (2% complex) compared to 120 inversions needed for noncoprecipitated PVP K 90 (1%).

EXAMPLE 9

A. In a 2-liter Hobart mixer, 100 g commercial Assert bisulfate was charged with 5 g Agrimer K 30 (PVP K 30). While the charge was thoroughly mixed in the dry state for a period of 1 hour, 5–7 ml deionized water was added over a period of 7–8 minutes, and agitation was continued for additional 30 minutes. The sample was dried in an electric oven for a period of 16 hours to produce a residual moisture content of 1%. The granules produced were evaluated for hardness and dissolution rates.

B. Part A was repeated except that in the place of 5 g Agrimer K 30, 9.8 g of the coprecipitate of Example 1 was used. The resulting granules were compared with those of Example 9. The granules of this example were harder, and dissolved in water in half the number of inversions; i.e., 100 inversions to dissolve at 1% active ingredient for the present sample as compared to 200 inversions required for that of sample A above.

EXAMPLE 10

Example 9A was repeated except that in the place of 5 g Agrimer K 30, 10 g of the coprecipitate of Example 3A was used. The granules from instant example were compared with those from Example 9A. The granules of this example were harder, and completely dissolved in water within ¼th the required number of inversions for 9A; (i.e., 50 inversions to dissolve 1% active ingredient for this example as compared to 200 required inversions for Example 9A).

EXAMPLE 11

Example 9A was repeated except that in the place of 5 g Agrimer K 30, 10 g of the coprecipitate of Example 4 was used. The granules obtained in this Example were compared with those of Example 9A. The present granules were harder, and fewer inversions were required to completely dissolve the granules in water; (i.e. 130 inversions to dissolve at 1% active ingredient for this example as compared with 200 for Example 9A.

EXAMPLE 12

The granules from Example 9A were loaded in a Tablet press with an average charge of 50 mg per tablet and tablets were produced at a compression pressure of 100 kg.

EXAMPLE 13

The granules from Example 10 were similarly loaded in a Tablet press with an average charge of 50 mg per tablet and tablets were produced at a compression pressure of 100 kg.

It was found that the tablets of this example were less friable, harder, and dissolved faster than those of Example 9A.

EXAMPLE 14

A. Cypermethrin (10 g) was charged in a 500 ml round bottom flask together with 90 g PVP K 30, 1 g sodium dodecyl benzene sulfonate and 250 g ethanol. The charge was kept at about 50° C. for a period of 4 hours. The solvent was evaporated at reduced pressure and the solid that remained was scraped from the flask for determining the rate of dispersion.

B. Example 14A was repeated except 90 g PVP K 30 was replaced with 50 g PVP K 30, and 45 g anhydrous citric acid. The resulting solid scraped from the flask was compared with that of part A and was also evaluated for ease of dispersion. The present solid (B) dispersed significantly faster than that obtained in sample A.

EXAMPLE 15

A. In a fluidized bed granulator, was charged 100 g of cypermethrin and 10 g sodium dodecylbenzene sulfonate solids. A 4-liter 25% aqueous solution of PVP K 30 was used as the fluid for granulation. The inlet air temperature was maintained at 45°–50° C. and after 2 hours, the resulting granules were evaluated for hardness, friability and ease of dispersion.

B. Part A was repeated except that solution of PVP was replaced by 4-liters of an aqueous solution containing 550 g PVP K 30 and 450 g anhydrous citric acid. The granules from this example (B) were harder, less friable and dispersed faster than those obtained in part A.

The substitution of any of the foregoing organic polybasic acids for citric acid in the above examples provides similar results. Although the optimum mole ratio of polymer to di-, tri- and tetra- carboxylic acids is indicated above, the ratio selected can depend on the option of the formulator as needs of application demand. Hence, where a dicarboxylic compound is selected and the ultimate use, eg. an agricultural product, does not demand the highest degree of attrition resistance, or a somewhat more rapid dissolution rate is not prohibitive, a mole ratio of polymer to acid within the lower portion of the above range may be selected.

What is claimed is:

1. The process of forming a binder for a bioactive chemical to produce an attrition resistant bioactive tablet having a dispersion rate less than 100 inversions/500 mg which comprises:
    (a) forming a mixture of an N-vinyl lactam polymer and a polybasic carboxylic acid in a mutual solvent at a mole ratio of from about 1:0.1 to about 1:10 based on polymer to carboxyl group,
    (b) coprecipitating said polymer and carboxylic acid at a temperature of from about 35° to 60° C. for a period of from about 2 to about 8 hours to form a complex,
    (c) drying to solid form said coprecipitate at a temperature below 60° C. by vacuum distillation or by freeze drying to remove solvent and
    (d) grinding said solids to an average particle diameter of from about 20 to about 350 microns.

2. The process of claim 1 wherein said particles are ground to an average particle diameter of from about 30 to about 250 microns.

3. The process of claim 1 wherein a chemically active component is intimately mixed with the particulate solids of step (d) and the resulting mixture compressed into tablet form.

4. The process of claim 1 wherein said chemically active component is sprayed into the mixture of the N-vinyl lactam polymer and polybasic carboxylic acid in a mutual solvent, thereby incorporating the active component in the resulting coprecipitate and the particulate solids of step (d) are compressed into tablet form.

5. The process of one of claims 3 and 4 wherein said chemically active component is selected from the group consisting of cypermethrin and methyl-6-(4-isopropyl-4-methyl-5-oxo-2-imidazolin-2-yl) toluate and isomers thereof.

6. The process of claim 1 wherein said polybasic carboxylic acid is citric acid.

7. The process of claim 1 wherein said N-vinyl lactam is a polymer of N-vinyl pyrrolidone.

8. The process of claim 1 wherein a buffering agent selected from the group of an alkali metal salt, an ammonium salt or an alkylammonium salt of said polybasic carboxylic acid is added in an amount up to 30 wt. % based on the coprecipitate of step (b).

* * * * *